(12) United States Patent
Connell et al.

(10) Patent No.: US 7,708,714 B2
(45) Date of Patent: May 4, 2010

(54) DIALYSIS CONNECTOR WITH RETENTION AND FEEDBACK FEATURES

(75) Inventors: Brian Connell, Evanston, IL (US);
Rafael A. Castellanos, Roselle, IL (US);
Bill Griswold, Bristol, WI (US); Daniel Marcquenski, Lake Zurich, IL (US);
Scott Ruddell, Gurnee, IL (US);
Timothy Seese, South Chicago Heights, IL (US)

(73) Assignees: Baxter International Inc., Deerfield, IL (US); Baxter Healthcare S.A., Zurich (CH)

( * ) Notice: Subject to any disclaimer, the term of this patent is extended or adjusted under 35 U.S.C. 154(b) by 1498 days.

(21) Appl. No.: 11/046,306

(22) Filed: Jan. 28, 2005

(65) Prior Publication Data
US 2005/0197646 A1    Sep. 8, 2005

Related U.S. Application Data

(63) Continuation-in-part of application No. 10/074,532, filed on Feb. 11, 2002, now Pat. No. 7,198,611.

(51) Int. Cl.
*A61M 1/00* (2006.01)
(52) U.S. Cl. .................................................. 604/30
(58) Field of Classification Search ................. 604/905, 604/415, 284, 256, 244, 206, 167.01–167.06, 604/165.01–165.04, 91, 88, 86, 83, 533; 285/331, 386
See application file for complete search history.

(56) References Cited

U.S. PATENT DOCUMENTS

| | | |
|---|---|---|
| 1,578,517 A | 3/1926 | Hein |
| 2,210,098 A | 8/1940 | Ravenscroft |
| 2,999,499 A | 9/1961 | Willet |
| 3,134,380 A | 5/1964 | Armao |
| 3,135,261 A | 6/1964 | Carroll |
| 3,502,097 A | 3/1970 | Muller |

(Continued)

FOREIGN PATENT DOCUMENTS

CA    1 105 959    7/1981

(Continued)

OTHER PUBLICATIONS

Nita's I.V. Standards of Practice, vol. 5 (Jan./Feb. 1982).

(Continued)

*Primary Examiner*—Manuel A Mendez
(74) *Attorney, Agent, or Firm*—K&L Gates LLP

(57) ABSTRACT

Apparatuses and methods for providing audio, visual and/or tactile feedback during assembly of two mating medical fluid connectors and a retention force are provided. The invention includes a first connector defining a first lumen and a second connector defining a second lumen. The first and second connectors are threaded together to enable the first lumen to initially communicate fluidly with the second lumen after the first and second connectors are engaged. The first connector defines a first engaging member and the second connector defines a second engaging member, the engaging members mating to provide (i) feedback indicating that a mating of the first and second connectors is at least substantially complete and (ii) a retention force tending to hold the first and second connectors together. An improved apparatus for releasing a sealed disinfectant is also provided.

12 Claims, 9 Drawing Sheets

U.S. PATENT DOCUMENTS

| | | | |
|---|---|---|---|
| 3,630,199 A | 12/1971 | Gangarosa et al. | |
| 3,659,602 A | 5/1972 | Cloyd | |
| 3,797,486 A | 3/1974 | Shaps | |
| 3,861,388 A | 1/1975 | Vaughn | |
| 3,974,832 A | 8/1976 | Kruck | |
| 3,976,073 A | 8/1976 | Quick et al. | |
| 3,986,508 A | 10/1976 | Barrington | |
| 3,994,293 A | 11/1976 | Ferro | |
| 4,005,710 A | 2/1977 | Zeddies et al. | |
| 4,019,512 A | 4/1977 | Tenczar | |
| 4,040,420 A | 8/1977 | Speer | |
| 4,079,738 A | 3/1978 | Dunn et al. | |
| 4,128,098 A | 12/1978 | Bloom et al. | |
| 4,149,535 A | 4/1979 | Volder | |
| 4,161,949 A | 7/1979 | Thanawalla | |
| 4,187,846 A | 2/1980 | Lolachi et al. | |
| 4,191,183 A | 3/1980 | Mendelson | |
| 4,214,779 A | 7/1980 | Losell | |
| 4,219,912 A | 9/1980 | Adams | |
| 4,256,106 A | 3/1981 | Shoor | |
| 4,257,416 A | 3/1981 | Prager | |
| 4,294,249 A | 10/1981 | Sheehan et al. | |
| 4,296,949 A | 10/1981 | Muetterties et al. | |
| 4,306,705 A | 12/1981 | Svensson | |
| 4,325,487 A * | 4/1982 | Libit | 215/330 |
| 4,328,802 A | 5/1982 | Curley et al. | |
| 4,329,987 A | 5/1982 | Rogers et al. | |
| 4,334,551 A | 6/1982 | Pfister | |
| 4,338,933 A | 7/1982 | Bayard et al. | |
| 4,354,490 A * | 10/1982 | Rogers | 604/403 |
| 4,362,156 A | 12/1982 | Feller, Jr. et al. | |
| 4,392,851 A | 7/1983 | Elias | |
| 4,405,312 A | 9/1983 | Gross et al. | |
| 4,432,765 A | 2/1984 | Oscarsson | |
| 4,439,193 A | 3/1984 | Larkin | |
| 4,457,749 A | 7/1984 | Bellotti et al. | |
| 4,508,367 A | 4/1985 | Oreopoulos et al. | |
| 4,511,359 A | 4/1985 | Vaillancourt | |
| 4,512,766 A | 4/1985 | Vailancourt | |
| 4,564,054 A | 1/1986 | Gustavsson | |
| 4,580,816 A | 4/1986 | Campbell et al. | |
| 4,607,868 A | 8/1986 | Harvey et al. | |
| 4,617,012 A | 10/1986 | Vallancourt | |
| 4,645,494 A | 2/1987 | Lee et al. | |
| 4,655,762 A | 4/1987 | Rogers | |
| 4,668,217 A | 5/1987 | Isono | |
| 4,673,400 A | 6/1987 | Martin | |
| 4,725,267 A | 2/1988 | Vaillancourt | |
| 4,752,292 A | 6/1988 | Lopez et al. | |
| 4,793,637 A | 12/1988 | Laipply et al. | |
| 4,820,288 A | 4/1989 | Isono | |
| 4,917,668 A | 4/1990 | Haindl | |
| 4,932,944 A | 6/1990 | Jagger et al. | |
| 4,946,445 A | 8/1990 | Lynn | |
| 4,964,855 A | 10/1990 | Todd et al. | |
| 4,981,469 A | 1/1991 | Whitehouse et al. | |
| 4,998,713 A | 3/1991 | Vaillancourt | |
| 4,998,921 A | 3/1991 | Vickroy et al. | |
| 5,069,225 A | 12/1991 | Okamura | |
| 5,100,394 A | 3/1992 | Dudar et al. | |
| 5,122,123 A | 6/1992 | Vaillancourt | |
| 5,153,489 A | 10/1992 | Unsworth et al. | |
| 5,158,554 A | 10/1992 | Jepson et al. | |
| 5,167,648 A | 12/1992 | Jepson et al. | |
| 5,171,234 A | 12/1992 | Jepson et al. | |
| 5,195,992 A | 3/1993 | Dudar et al. | |
| 5,199,947 A | 4/1993 | Lopez et al. | |
| 5,200,575 A | 4/1993 | Sheehan | |
| 5,290,254 A | 3/1994 | Vaillancourt | |
| 5,344,414 A | 9/1994 | Lopez et al. | |
| 5,377,694 A | 1/1995 | Bark | |
| 5,393,101 A | 2/1995 | Matkovich et al. | |
| 5,401,066 A | 3/1995 | Remsburg | |
| 5,518,276 A | 5/1996 | Gunderson | |
| 5,549,583 A | 8/1996 | Sanford et al. | |
| 5,607,392 A | 3/1997 | Kanner | |
| 5,620,427 A | 4/1997 | Werschmidt et al. | |
| 5,688,254 A | 11/1997 | Lopez et al. | |
| 5,855,398 A | 1/1999 | Reinholz | |
| 5,954,708 A | 9/1999 | Lopez et al. | |
| 5,971,958 A | 10/1999 | Zhang | |
| 6,086,575 A | 7/2000 | Mejslov | |
| 6,183,465 B1 | 2/2001 | Meier et al. | |
| 6,193,283 B1 | 2/2001 | Pickett, Jr. et al. | |
| 6,193,697 B1 | 2/2001 | Jepson et al. | |
| 6,234,544 B1 | 5/2001 | Bartholomew | |
| 6,406,470 B1 | 6/2002 | Kierce | |
| 6,508,810 B1 | 1/2003 | Ouchi et al. | |
| 6,589,251 B2 | 7/2003 | Yee et al. | |
| 6,612,622 B2 | 9/2003 | Andre et al. | |
| 6,652,509 B1 | 11/2003 | Helgren et al. | |
| 6,673,059 B2 | 1/2004 | Guala | |
| 7,316,679 B2 * | 1/2008 | Bierman | 604/535 |
| 2002/0010437 A1 | 1/2002 | Lopez et al. | |
| 2002/0023504 A1 | 2/2002 | Austin | |
| 2002/0082586 A1 | 6/2002 | Finley et al. | |
| 2002/0095210 A1 | 7/2002 | Finnegan et al. | |
| 2003/0006610 A1 | 1/2003 | Werth | |
| 2003/0144647 A1 | 7/2003 | Miyahara | |
| 2003/0176852 A1 | 9/2003 | Lynch et al. | |
| 2003/0184090 A1 | 10/2003 | Guala | |
| 2004/0034334 A1 | 2/2004 | Ruddell et al. | |
| 2004/0087986 A1 | 5/2004 | Ott | |
| 2004/0238776 A1 | 12/2004 | Peters et al. | |

FOREIGN PATENT DOCUMENTS

| | | |
|---|---|---|
| DE | 84 25 197 | 10/1985 |
| EP | 0 113 677 | 8/1984 |
| EP | 1243280 | 9/2002 |
| EP | 1331020 | 7/2003 |
| GB | 2343723 | 5/2000 |
| WO | WO94/23775 | 10/1994 |
| WO | WO2004/033023 | 4/2004 |
| WO | WO2004/071557 | 8/2004 |

OTHER PUBLICATIONS

Baxter, Closed Drainage Bag, Cat. No. 5912 (Oct. 1993).
Baxter, Urine Sampling Unit, Cat. No. 9680 (Feb. 1992).
Travenol Labs. Inc., Keeping your integrity intact, Mini-Bag Underfill Viaflex Containers (Undated).
Home I.V. Therapy Standards of Practice, Journal of the National Intravenous Therapy Ass. (Apr. 1984).
Travenol, the Continu-Flo Administration System (Undated).
McGaw Labs., We don't overlook the smallest detail at McGaw, American Journal of Hospital Pharmacy, vol. 26 (Jan. 1969).
Contamination rates and costs associated with the use of four intermittent intravenous infusion systems, American Journal of Hospital Pharmacy, vol. 36 (Nov. 1979).
Evaluation of piggyback administration sets, D.W. Raisch, K.T. Johnson. C. Roth, American Society of Hospital Pharmacy (1977).
International Search Report for International Patent Application No. PCT/US2005/038424 that corresponds to the present application and of which the references cited above as cited therein.

* cited by examiner

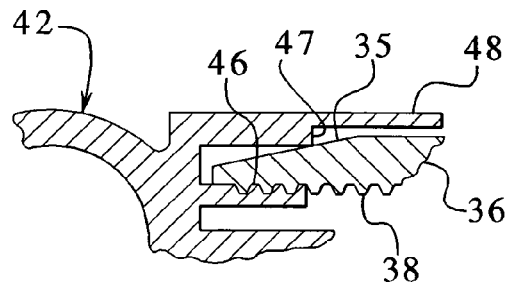
FIG.1B
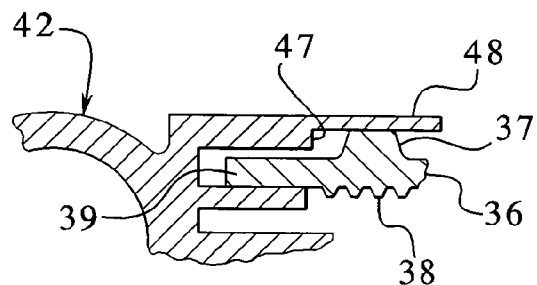
FIG.1C
FIG.2
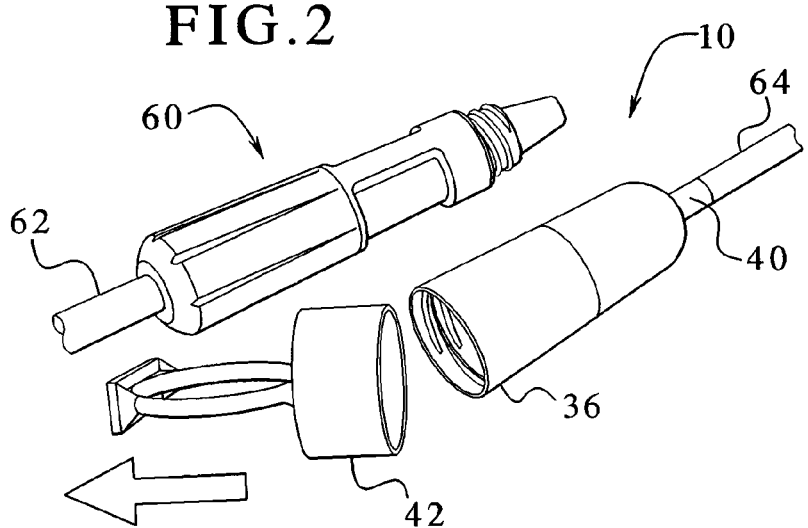
FIG.3
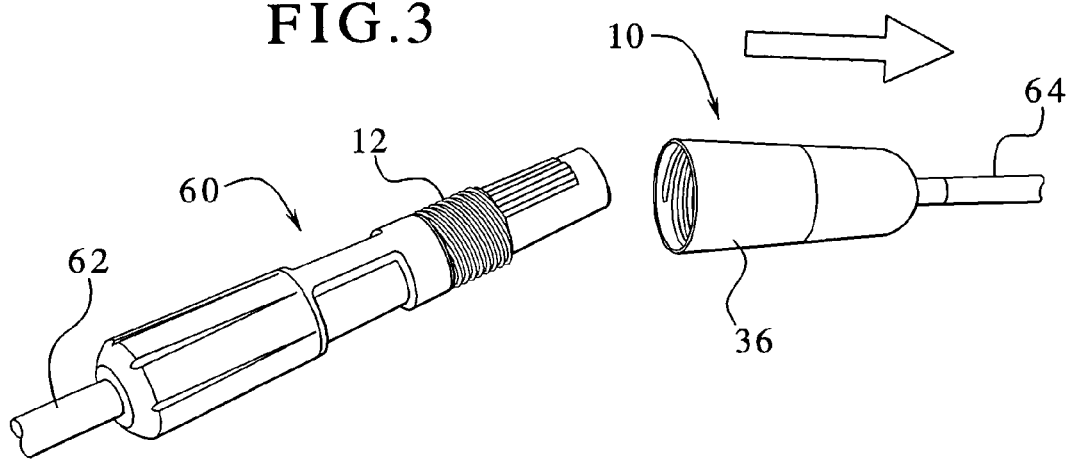

DIALYSIS CONNECTOR WITH RETENTION AND FEEDBACK FEATURES

PRIORITY CLAIM

This application is a continuation-in-part application of U.S. Non-Provisional patent application Ser. No. 10/074,532, filed Feb. 11, 2002, now U.S. Pat. No. 7,198,611, entitled "Dialysis Connector And Cap Having An Integral Disinfectant", the entire contents of which are hereby incorporated by reference and relied upon.

BACKGROUND OF THE INVENTION

The present invention relates generally to medical treatments. More specifically, the present invention relates to medical connectors for use in medical treatments, such as Peritoneal Dialysis ("PD").

Due to disease, insult or other causes, a person's renal system can fail. In renal failure of any cause, there are several physiological derangements. The balance of water, minerals and the excretion of daily metabolic load is no longer possible in renal failure. During renal failure, toxic end products of nitrogen metabolism (urea, creatinine, uric acid, and others) can accumulate in blood and tissues.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving. One who has failed kidneys could not continue to live without replacing at least the filtration functions of the kidneys.

PD uses a dialysis solution or dialysate, which is infused into a patient's peritoneal cavity. The dialysate contacts the patient's peritoneal membrane in the peritoneal cavity. Waste, toxins, and excess water pass from the patient's bloodstream through the peritoneal membrane and into the dialysate. The transfer of waste, toxins, and water from the bloodstream into the dialysate occurs by diffusion and osmosis because there is an osmotic gradient across the peritoneal membrane. The spent dialysate is drained from the patient's peritoneal cavity to remove the waste, toxins and water from the patient. New dialysate replaces the spent dialysate and the process repeats.

During dialysis therapy, a dialysis fluid exchange generally includes draining spent dialysis fluid from the peritoneal cavity and filling the peritoneal cavity with fresh dialysate. Keeping track of the amounts or volumes of dialysis solution drained from and supplied to the peritoneal cavity is important for proper dialysis therapy. A typical amount of dialysate solution drained from and supplied to the peritoneal cavity of an adult during an exchange can be roughly two to three liters. Dialysis fluid exchanges have been performed manually, usually by the patient, or automatically, by an automated dialysis machine.

In the manual PD technique, known as Continuous Ambulatory Peritoneal Dialysis ("CAPD"), a catheter is implanted into the peritoneal cavity of the patient. A dialysis solution ("dialysate") is introduced through the catheter into the peritoneal cavity of a patient. Typically, a container of the dialysate connects to a connector, which in turn couples to the catheter. To start the flow of dialysate into the peritoneal cavity, a clamp on a tube connecting the container to the connector is loosened or a valve is opened. In many cases the container is located vertically above the patient and gravity fed into the peritoneal cavity.

In the Automated Peritoneal Dialysis technique ("APD"), dialysis machines use one or more fluid pumps to perform the dialysate exchanges. The pump pumps spent dialysate fluid out of the peritoneal cavity during the drain mode and pumps dialysate into the cavity during the fill mode.

In either PD technique, once the dialysate reaches the patient, dialysis of urea, toxic waste and the like takes place between the dialysate and the blood passing through blood vessels in the peritoneum, which is the lining of the peritoneal cavity. The dialysate remains in the peritoneal cavity for several hours. Thereafter, the dialysate is removed from the peritoneal cavity carrying with it diffused breakdown products from the blood. In CAPD, one method for removing the spent dialysate is to lower the dialysate container outside of the body and let the dialysate drain into the container.

The spent container is disconnected and discarded, wherein a new container of dialysate fluid is attached and the process is repeated. This process may be repeated several times or continuously repeated. Because many patients perform the PD (CAPD or APD) procedure themselves, it is important that the connector which connects the dialysate container to the catheter is easy to use and provides a secure connection.

A frequent problem that occurs with PD is peritoneal infection or peritonitis which can readily occur given the repeated disconnecting and reattaching of the dialysate containers. Peritonitis results if connections are made between the peritoneal catheter and the connector communicating with the dialysis container in a manner that permits even a very small number of microorganisms to enter the catheter. The microorganisms will be flushed into the peritoneal cavity. Peritonitis can occur even when extreme caution is observed in making and unmaking the connections. Peritonitis can be painful and can temporarily diminish the hydraulic permeability of the peritoneal membrane, rendering the renal treatment less successful.

Methods to prevent peritonitis have included thoroughly cleansing the connector and the tube connecting the dialysate container before the connection is made. For instance, the connector can be immersed in povidone iodine, betadine or other type of disinfectant. These methods however are messy, time consuming, effort consuming, inconsistent and may be subject to overkill in order to achieve consistently effective results. Hospital workers, as another precaution, typically wear sterile rubber gloves to prevent or guard against any possible peritoneal invasion of bacteria. However, the spread of contamination can still occur due to, for example, a cut in the glove or other like condition.

Accordingly, the frequent connections that must be made and broken between the catheter residing in the peritoneal cavity and a succession of dialysate containers has created a need to ensure the sterilization of connectors used in performing CAPD and APD. The connections need to be substantial enough to not loosen or become disconnected during dialysis. Patients with poor physical strength and manual dexterity however need to be able to engage and disengage the connectors with relative ease.

A continuing need therefore exists to provide a simple and effective method and apparatus for performing PD, including CAPD and APD both in hospitals and at a patient's home.

SUMMARY OF THE INVENTION

The present invention relates to a connector and a cap that are easily and readily attachable to a dialysate container and a catheter inserted into a patient's peritoneal cavity. The connector and the cap enable the dialysate to be readily transported between the container and the peritoneal cavity while minimizing the potential of contamination therein due to, for example, handling during use.

To this end, in an embodiment of the present invention, a connector includes a shell that encloses a cap. The cap houses a slit septum. The cap also includes a sealed disinfectant within an interior receptacle. The seal in an embodiment is a cross-linked elastomeric seal, e.g., a silicone seal. In one embodiment, the disinfectant includes a povidone iodine or PVP-I. The connector is also initially packaged including a tip protector that encloses the shell/cap assembly and provides a barrier to microbial contamination prior to use.

In another embodiment of the present invention, a cap for use in a connector making a resealable fluid path is provided. The cap includes a body that defines a fluid flow passage and a disinfectant receptacle. The receptacle houses the disinfectant. A seal is disposed within the body. The seal seals the disinfectant between the seal and the receptacle.

In an embodiment, the body defines an opening that receives a fluid communication member. The fluid communication member is capable of displacing the seal when the body receives the member.

In an embodiment, the disinfectant disperses between an outer wall of the fluid communication member and an inner wall of the body when the seal is displaced.

In an embodiment, the body defines outer threads.

In an embodiment, the outer threads engage mating threads of a shell and enable the shell to translate with respect to the body. The translating shell causes a sealed end of the body to be pierced.

In an embodiment, the body defines inner threads.

In an embodiment, the inner threads engage mating threads of a fluid communication member and enable the member to translate with respect to the body. The translating member causes the seal to be displaced.

In an embodiment, the seal is moveable.

In an embodiment, the body includes a tube portion that defines the fluid flow passage. The disinfectant receptacle resides about the tube portion.

In an embodiment, a portion of the passage is sized to house a member that deforms to seal about a tube.

In an embodiment, the member automatically closes when the tube is removed from the member.

In still another embodiment of the present invention, a connector for making a resealable fluid path is provided. The connector includes a cap that defines a fluid flow passage. The cap seals an amount of disinfectant, such as a continuous quantity thereof. A shell moveably engages the cap. The shell includes a fluid communication member. The fluid communication member is capable of piercing a sealed end of the cap and fluidly communicating with the fluid flow passage when the shell moves with respect to the cap.

In an embodiment, the disinfectant includes povidone iodine.

In an embodiment, the connector includes a tip protector that engages the shell.

In an embodiment, the shell attaches to a fluid line running to a dialysate container and the cap attaches to a fluid line running to a patient.

In an embodiment, the sealed end of the cap includes a slit septum.

In an embodiment, the connector includes an elastomeric seal that seals the disinfectant about the fluid flow passage.

In still another embodiment of the present invention, a method for providing a sterile connection of a dialysate line is provided. The method includes providing a cap that has a passage and maintains a seal that houses a disinfectant. A first member connects to a first end of the cap. The first member then fluidly communicates with a first dialysate line. A second member connects to a second end of the cap so as to displace the seal and the disinfectant. The second member then fluidly communicates with a second dialysate line.

In an embodiment, connecting the first member includes moving the first member so as to pierce a sealed end of the cap, which places the first member in fluid communication with the second member.

In an embodiment, the sealed end of the cap seals about the first member when the first member pierces the sealed end.

In an embodiment, the sealed end of the cap reseals when the first member is removed from the cap.

In an embodiment, rupturing the seal includes threading the second member into the cap and exerting pressure on the seal.

In an embodiment, connecting the second member includes displacing the disinfectant between the cap and the second member.

In an embodiment, the method further includes maintaining the disinfectant between the cap and the second member after the seal is displaced.

In an embodiment, the method includes removing the first member from the cap such that the sterile connection between the cap and the second member is maintained.

In an embodiment, the method includes removing a tip protector and connecting the second member in place of the tip protector.

In still another embodiment of the present invention, a method for providing PD is provided. The method includes the steps of providing a first member in fluid communication with a dialysate container, a second member in fluid communication with a peritoneal cavity of a patient, and a cap that has a sealed first end, a second end, a passage and maintains a seal that houses a disinfectant; connecting the first member to the sealed first end of the cap; connecting the second member to the second end of the cap so as to displace the seal and the disinfectant thereby causing the first member to pierce the sealed first end of the cap; filling the peritoneal cavity with an amount of fresh dialysate fluid; and removing the first member to automatically reseal the first end of the cap.

In an embodiment, the method includes removing an amount of spent dialysate fluid from the peritoneal cavity prior to filling the peritoneal cavity with the fresh dialysate fluid.

In an embodiment, the method includes connecting another first member to the first end, removing spent dialysate fluid from the peritoneal cavity and refilling the peritoneal cavity with fresh dialysate fluid.

In different embodiments, the filling and removing steps are performed manually or automatically.

In any of the different embodiments described above, the end of the transfer set or member that moves the seal to displace the disinfectant is contoured to break or move the seal readily so that the seal may be provided and maintained without too much difficulty. The seal is configured to retain the disinfectant under extreme conditions of steam or other type of sterilization technique, but which will also rupture easily to displace disinfectant when needed. In one embodiment, the transfer set end or member that moves or ruptures the seal is contoured so that the force necessary to move the seal fully to displace the disinfectant fully is reduced. Also, the tendency of the seal to adhere to the end of the transfer set or member is lessened.

In any of the different embodiments described above, a shell of the dialysis connector (e.g., leading from the dialysis supply) and a portion of the transfer set (leading from the patient) can have mating retention and tactile feedback features. Such features help to ensure that the connector and transfer set are tightened enough but not overly tightened. The features can also provide audio, visual and/or tactile feedback to the patient so that the patient knows when it is safe to stop attempting to connect the dialysate connector to the transfer set.

In one embodiment, the shell of the connector includes teeth that mate with a plurality of ramps disposed on a rib or ring of the transfer set. The ramps are alternatively ribs or other shaped protrusions, which provide a different tactile feedback to the patient when the connector and transfer set are mated. There may be relatively few ramps or the transfer set may include a relatively large number of ramps or protrusions that are spaced apart closely enough from each other to form a ratchet-like fit between the dialysate connector and the patient's transfer set. In another embodiment, the shell includes a female undercut that threads over a bump protruding from the ring or rib of the transfer set.

In a further alternative embodiment, the dialysate connector or the transfer set is provided with an o-ring or gasket. The o-ring or gasket can have one of many different cross-sections and can be sealed axially or radially between the shell of the connector and the transfer set. Alternatively, the transfer set is provided with cantilevers or protrusions that increase a friction force as the connector is threaded over the transfer set. Still further, the shell of the dialysate connector can be provided with one or more arms or snap-fitting extensions that snap-fit onto a portion of the transfer set when the connector and transfer set are mated fully.

It is therefore an advantage of the present invention to provide a dialysis connector that eliminates the need for the use and therefore handling of an additional cap to seal a catheter subsequent to use.

Moreover, an advantage of the present invention is to provide a dialysis connector that reduces the likelihood of peritonitis.

Another advantage of the present invention is to provide a dialysis cap that remains attached to a catheter set after use.

Still another advantage of the present invention is to provide a connector and a cap therefore having a septum that automatically reseals upon removal of the cap from a shell that couples to the dialysate container.

A further advantage of the present invention is to provide a dialysis connector employing a sealed disinfectant in conjunction with a releasable and resealable cap, which effectively minimizes the spread of microbial contamination to a catheter transfer set, and thus to the patient, during dialysis therapy.

Yet another advantage of the present invention is to provide a cap for use in PD, including CAPD and APD that contains a disinfectant and that cannot spill the disinfectant when a tip protector is removed.

Yet a further advantage of the present invention is to provide a cap for use in CAPD and APD that contains a continuous amount of a disinfectant and does not require an absorbent material to hold the disinfectant.

Still further, an advantage of the present invention is to provide a resealable cap enclosed within a protective shell prior to insertion of a catheter set.

Further still, it is an advantage of the present invention to provide a dialysis connector and patient transfer set that when matted fully provide visual, audio and/or tactile feedback to the patient.

It is yet a further advantage of the present invention to provide a disinfectant seal and moveable member interface that reduces an amount of force that the member needs to provide to move the seal fully and reduces a likelihood that the seal will adhere to the moved member.

Additionally, it is an advantage of the present invention to provide a resealable cap having a sealed disinfectant that displaces across threads of the cap and the transfer set.

Additional features and advantages of the present invention are described in, and will be apparent from, the following Detailed Description of the Invention and the Figures.

BRIEF DESCRIPTION OF THE FIGURES

FIG. 1B is a schematic sectional view showing an embodiment of an interface between the shell and the tip protector.

FIG. 1C is a schematic sectional view showing another embodiment of an interface between the shell and the tip protector.

FIG. 2 is a perspective view illustrating a part of the process for connecting the connector and cap of the present invention to a transfer set, which connects a catheter to a patient.

FIG. 3 is a perspective view illustrating another part of the process for connecting the connector and cap of the present invention to a transfer set, which connects a catheter to a patient.

DETAILED DESCRIPTION OF THE INVENTION

Medical Fluid Connector with Disinfectant

The present invention provides a connector and a cap therefore that includes a disinfectant for any system requiring a connection, such as a connection of a first length of tubing or other conduit to a second length of tubing or other conduit, such as for PD. The present invention provides a safe and easy connection and method for introducing a disinfectant for a user/patient. The connector and cap therefore do not create a mess and do not make the user/patient perform special handling in order not to spill the disinfectant contained therein.

The method and apparatus for the present invention can be used to perform Continuous Ambulatory Peritoneal Dialysis ("CAPD") and Automated Peritoneal Dialysis ("APD"), collectively referred to herein as Peritoneal Dialysis ("PD"). It should be appreciated, however, that the connector and cap and method for using same can be used in a variety of other applications, particularly applications that insert a medical fluid into the body of a patient.

Figure 1A:
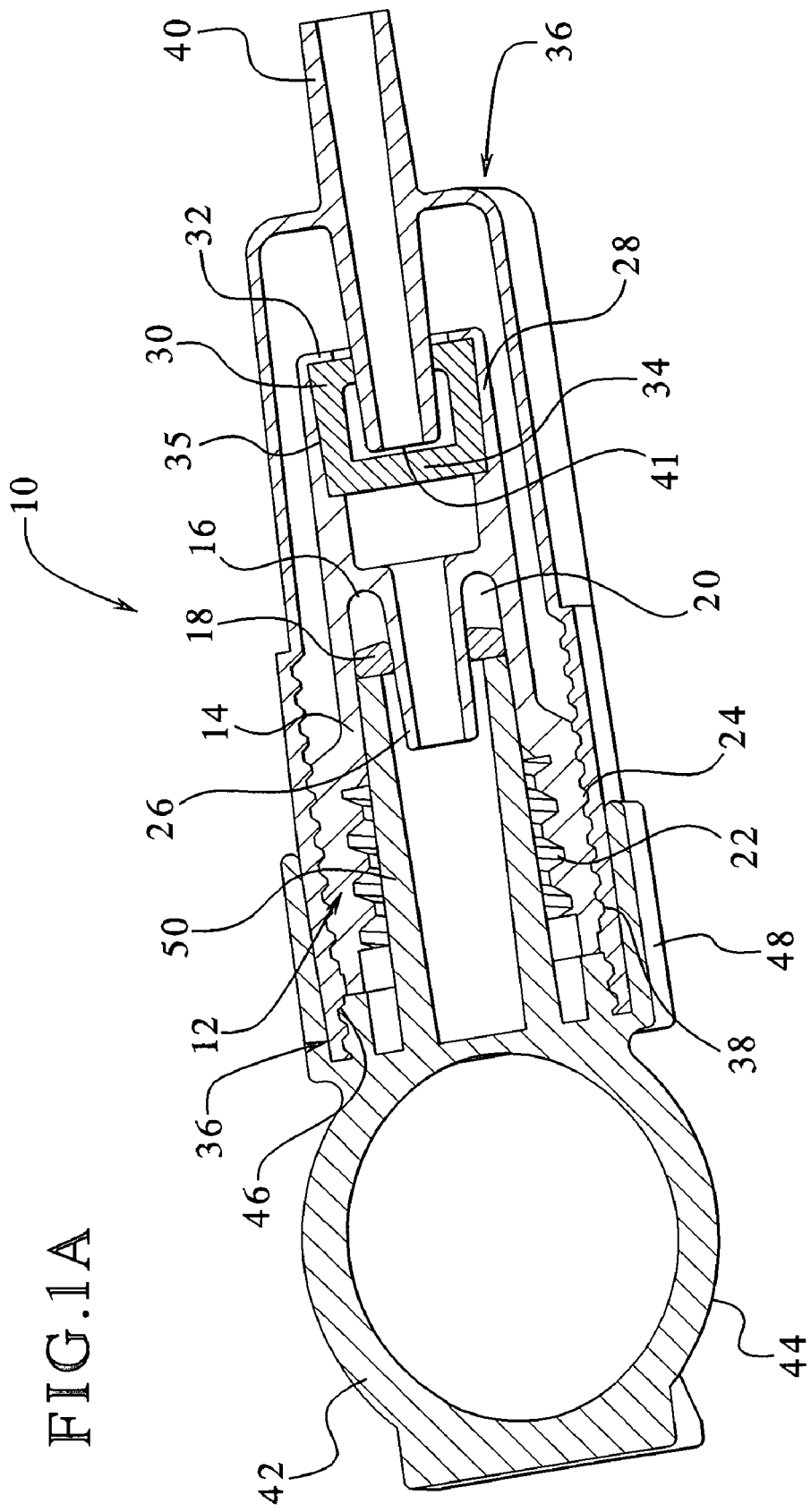
FIG. 1A is a perspective view of one embodiment of the dialysis connector and cap therefore of the present invention.

Referring now to the figures, and in particular to FIGS. 1A to 1C, a connector 10 of the present invention is illustrated. FIG. 1A illustrates that the connector 10 includes a cap 12. Generally, the components of the present invention, including the cap 12, are made of a plastic material such as polyethylene, polypropylene, nylon, polystyrene, polyester, PVC, a blend of various plastics or any other plastic or synthetic material that is capable of being washed and sterilized or substantially sterilized. As is illustrated below, certain components of the connector 10 seal to other components. These sealing components are generally made from compressible materials such as compressible rubber, e.g., silicone or the like.

The components of the connector 10 are constructed into desired shapes via any known method for producing plastic or rubber pieces, such as a molding process, e.g., an injection molding process. The compressible or rubber pieces may alternatively be cut and/or stamped from a larger piece of the compressible or rubber material. In alternative embodiments, one or more of the components, i.e., the plastic components, may alternatively be constructed from a metal, e.g., a non-corrosive metal such as stainless steel or aluminum, and may be formed via any known method of forming or stamping same.

The cap 12 includes a body 14 that is injection molded or blow molded to define a desired shape. Although FIG. 1A shows one embodiment of the connector 10 and the cap 12, the body 14 of the cap 12 may be made in a variety of different shapes and sizes to mate with and/or work with various systems for introducing medical fluids into a patient. The various systems can be provided by other manufacturers or by the assignee of this invention. In one embodiment, the body 14 defines the following components or features.

The body 14 defines at least one receptacle 16. The receptacle 16 is a well or other liquid containing shape that encompasses a void except for a sealable side. The body 14 can define a variety of different receptacles 16; however, FIG. 1A shows an embodiment wherein the body 14 defines a single receptacle 16. A seal 18 encloses or caps off the receptacle 16. The seal 18 in an embodiment is a cross-linked elastomeric seal made from silicone. The seal may alternatively be made from any other type of rubber or compressible material such as neoprene, vinyl, viton, buna-n, butyl, EPDM, latex or the like.

The seal 18 can be made from solid or sponge rubber. In an embodiment, the seal 18 may be clear so that the user or patient can see a disinfectant 20 housed between the seal and the receptacle 16. In an embodiment, the seal 18 is coated with or impregnated with a disinfectant, which acts to further sterilize the connector 10.

In an embodiment, the seal 18 compresses against the walls of the receptacle 16, so that the disinfectant 20 residing within the receptacle 16 in any suitable form and/or manner cannot initially escape, even if the cap 12 of the connector 10 is turned so that the seal 18 faces downward and even if the patient or user moves, manipulates, shakes or otherwise causes the disinfectant 20 to move within the receptacle 16.

In an embodiment, the seal 18, compressed within the walls of the receptacle 16, is translatable so that the seal 18 can move towards an end of the receptacle 16. The method for translating the seal 18 is set forth in detail below in connection with FIGS. 3 to 7. In an alternative embodiment, the seal 18 is thin or otherwise frangible, e.g., is constructed from a thin plastic or metal-coated plastic sheet. The sheet is designed to rip when the patient or user applies pressure to the sheet, wherein the disinfectant flows through the ruptured sheet of the seal 18. In the alternative embodiment, the seal 18 would not compress against the walls of the receptacle 16; rather, a suitable adhesive would be used to secure the seal 18 to the receptacle 16, or the seal 18 could be adhered to the receptacle 16 via a known heat-shrinking or heating process.

The disinfectant 20 is adaptable to be any suitable type, form and/or amount of disinfectant that can sterilize or substantially sterilize plastic, rubber, metal or other like materials. In an embodiment, the disinfectant 20 is composed of povidone iodine. It should be appreciated that the povidone iodine can be provided in any suitable form and/or amount thereof In an embodiment, a povidone iodine gel may have been subjected to gamma irradiation, steam sterilization and/or ethylene oxide.

In another embodiment, the disinfectant is or includes iodine-containing antimicrobials. In a further embodiment, the disinfectant uses or includes a povidone iodine (not in gel form) that is or may be subjected to gamma irradiation and/or steam sterilization. In still another embodiment, the disinfectant is or includes betadine. It should be appreciated that the disinfectant 20 of the present invention can alternatively be any desired disinfectant known to those of skill in the art.

The body 14 of the cap 12 also in an embodiment defines internal threads 22 and external threads 24. In the illustrated embodiment, the internal threads 22 and external threads 24 reside on the same end of the cap 12. The purpose of the inner and outer threads will be shown below. It is important to note, however, that the relative relationship between the internal threads 22 and the external threads 24 is not important to the operation of the present invention. In general, the body 14 of the cap 12 enables the first member to move along the central axis of the body 14 via one of the set of threads. The body 14 of the cap 12 also enables a second member to move along the central axis of the body 14. It is not important which member moves by engaging the internal threads 22 and which member moves in the other direction by engaging the external threads 24. An important aspect of the present invention, rather, is that two separate members may move inward and outward relative to the body 14 of the cap 12.

The inner threads 22 and the outer threads 24 may have any thread pitch desired by the implementor of the present invention. In the illustrated embodiment, the external threads 24 are slightly tapered, for example, at about one degree. In an alternative embodiment, the threads are straight, such as in a lead screw or ball screw. In the illustrated embodiment, the external threads 24 enable one member to translate relative to another, wherein the member eventually bottoms out or has a limited range of travel with respect to the external threads 24. Likewise, the inner threads 22 may be straight threads that allow a member to rotate freely in and out of the body 14 or the inner threads 22 may be tapered such that the member bottoms out as it inserts into the body 14.

The body 14 defines a passage 26 that enables a medical fluid such as a dialysate to move from one end of the cap 12 to another. The passage 26 can alternatively be the opening defined by the inner threads 22 and does not have to include the reduced tubing piece illustrated as the passage 26 in FIG. 1A. The passage 26, however, is sized to have approximately the same inner diameter as the tubes or catheters carrying the dialysate back and forth from a dialysate container and the peritoneal cavity of the patient.

In the illustrated embodiment, the body 14 defines a housing 28 at an end opposing the internal and external threads 22, 24. The housing 28 is sized to hold a septum 30. The housing 28 is swaged to the septum 30 or otherwise holds the septum 30 in a snug manner. The septum 30 cannot move in either axial direction relative to the body 14. The body 14 defines an end wall 32 having a smaller inner diameter than that of the housing 28, which also holds the compressible septum 30 in place. A suitable adhesive may also be employed to hold the septum 30 within the housing 28.

In an embodiment, the septum 30 is cylindrical as is the body 14 and the connector 10 in general. However, the septum 30, the body 14, and the connector 10 can each have alternative shapes such as being square or rectangular.

The septum 30 in an embodiment is made of a compressible or rubber material. The septum can be made from any type of rubber, including any of the above listed rubbers. As is well known in the art, the septum 30 defines a slit (not illustrated) which enables a tube or other type of fluid communication member to pass through a back wall 34 of the septum 30. The septum 30 in the illustrated embodiment generally defines a cap- or nut-shaped rubber or otherwise compressible piece having the back wall 34 and a cylindrical side wall 35 that extends from the back wall 34. The nut-shaped or cap-shaped septum in an embodiment is made as one piece, wherein the slit is made in the back wall 34. A tube or fluid communication member then inserts and resides inside a hollow chamber defined by the septum 30 and at some point is able to pass through the back wall 34.

In the illustrated embodiment, the connector 10 is configured so that the external threads 24 of the body 14 mate with internal threads of a shell 36. The shell 36 is a plastic or metal piece and may be of the same material as the body 14 of the cap 12. The shell 36 defines the internal threads 38 that mate with the external threads 24 of the body 14. The shell 36 can thus translate in either axial direction relative to the body 14 by rotating in a clockwise or counterclockwise direction about the body 14.

The shell 36 defines a tube or port 40, which in an embodiment is integrally formed with the shell 36, e.g., through an injection molding or blow molding process. The tube 40 extends inwardly into a cavity defined by the shell 36 and into the body 14 of the cap 12 through an opening defined by the end wall 32 of the body 14. The tube 40 also inserts into the cavity defined by the septum 30. When the shell 36 rotates about the outer threads 24 of the body 14 to a packaging position, an end 41 of the tube 40 abuts or is directly adjacent to the back wall 34 of the septum 30. For example, there may be a gap of about 0.010 in. (0.25 mm.) between the end 41 of the tube 40 and the back wall 34 of the septum 30.

The tube or port 40 also extends outwardly from the shell 36. The tube or port 40 sealingly connects to a tube (not illustrated) that runs to a dialysate container or a container housing the medical fluid that transfers through the connector 10 of the present invention. In an embodiment, the tube connecting to the dialysate bag press fits or sealingly fits over the port 40 in such a way that the dialysate does not leak from the interface of the flexible tube running to the dialysate container and the port 40. The tube of the dialysate bag can also connect to the port 40 via a solvent bond.

It should be appreciated that the dialysate is generally transferred back and forth, to and from, the dialysate container under its own weight and generally does not require an external pump or pressure system to drive the flow. Therefore, the fluid is not under substantial pressure and the seal required for the port 40 is not difficult to achieve. In an alternative embodiment, a hose clamp or other type of releasably fastenable device may be used to bolster the seal made between the flexible tube running to the dialysate bag and the port 40. Such interface is made readily and without requiring the patient or user to have an excessive amount of strength or to perform overly intricate operations.

A tip protector 42 fits over the shell 36 and at the same time fits into the interior cavity defined by the internal threads 22 of the body 14. The tip protector 42 is made in an embodiment of any of the plastic materials described above. The tip protector 42 defines a ring or handle 44 that enables the user or patient to remove the tip protector 42 from the shell 36 to begin using the connector 10. That is, the connector 10 is initially packaged with the tip protector 42. The first time the user or patient uses the tip protector 42, the user or patient removes the tip protector and discards it.

The tip protector 42 serves a number of purposes in protecting the connector 10 prior to use. The tip protector 42 provides a microbial barrier. The tip protector 42 disallows bacteria and other harmful airborne agents from entering the body 14 of the cap 12 prior to use. Just before attaching the cap 12 to a mating connector (see mating connector 60 in FIGS. 2 through 7), the patient or operator removes the tip protector 42. In this way, the inside of the body 14 of the cap 12 is only exposed to open air for a very short amount of time.

In an embodiment, for example, when the connector 10 is to be used for CAPD, the tip protector 42 also sets the shell 36 at the appropriate distance relative to the body 14 for packaging the connector 10. That is, the tip protector 42 helps to set the end 41 of the tube 40 of the shell 36 directly adjacent to the back wall 34 of the septum 30.

Prior to use, the tube 40 does not insert into or open up the slit (not illustrated) in the back wall 34 of the septum 30. However, it is desirable not to have the end of the tube or port 40 too far away from the back wall 34 of the septum 30 upon packaging the connector 10 for a couple of reasons. First, it is desirable to package the connector 10 in as small a space as possible. If the connector 10 is packaged so that the end 41 resides away from the back wall 34, then the connector 10 is longer in an axial direction than it needs to be. Second, it is desirable not to make the user or patient rotate the shell 36 more than is necessary to insert the tube 40 through the slit of the back wall 34 of the septum 30 to begin using the connector 10.

FIGS. 1A and 1B illustrate that the tip protector 42 in an embodiment defines threads 46 that engage some of the internal threads 38 of the shell 36. The shell 36 only threads into the tip protector 42 so far before the shell 36 bottoms out against a cylinder 48 defined by the tip protector 42. FIG. 1B illustrates that in an embodiment, the outside of the shell 36 includes a taper 35 at the end of the portion of the shell 36 defining the threads 38. As the tip protector 42 threads into the shell 36, the taper 35 increasingly presses against the inside of the cylinder 48. In an embodiment, the cylinder 48 of the tip protector 42 defines a stepped portion 47 that facilitates the engagement between the taper 35 of the shell 36 and the tip protector 42.

Thus, when the connector 10 is packaged, the tip protector 42 can be placed against or abutted against the body 14 of the cap 12 before the shell 36 threads onto the body 14 and onto the threads 46 of the tip protector 42. The shell 36 threads over the external threads 24 of the body 14 and passes or translates past the body 14 a desired distance defined by the threads 46 of the tip protector 42. It is at this point that the end 41 of the tube 40 abuts or is directly adjacent to the end wall 34 of the septum 30.

It should be appreciated that the cylinder 48 of the tip protector 42 is not threaded and does not threadingly engage the shell 36 so that the cylinder 48 simply slides over and translates relative to the shell 36. It should also be appreciated that to remove the tip connector 42, the user holds the shell 36 and rotates the ring 44 a number of turns.

FIG. 1C illustrates an alternative embodiment that is used, for example, when the connector 10 performs APD. The tip protector 42 simply slides and possibly slightly press fits onto or into the body 14 of the cap 12. Here, the tip protector 42 does not define the threads 46. The shell 36 may or may not be tapered and may contain a stepped member 37, wherein the member 37 is intended to slightly frictionally engage the inner wall of the cylinder 48. The internal threads 38 of the shell 36 stop before reaching the inner portion 39 of the shell 36 that abuts the tip protector 42.

When the connector is initially packaged, the body 14 cannot move relative to the shell 36 until the tip connector 42 is removed. This is important to ensure that the seal 18 is not ruptured or displaced prior to using the connector 10. The tip protector 42 also includes an inner extension 50 that extends into the chamber created by the internal threads 22 of the body 14. The extension 50 extends so that it abuts or is directly adjacent to the seal 18. This ensures that prior to use, the seal 18 does not loosen and move away from the receptacle 16 to thereby create a leaky connector 10. Thus, it should be appreciated that the tip connector 42 enables the connector 10 to be handled and shipped without destroying the seal 18 and/or losing the disinfectant 20 maintained by the seal 18.

Referring now to FIGS. 2 and 3, one embodiment for connecting the connector 10 of the present invention to a mating connector 60 is illustrated. The connector 10 may be adapted to operate with many different types of connectors or devices that provide a catheter 62 that inserts into the peritoneal cavity of the patient. In an embodiment, the connector 10 is adapted to attach to a transfer set that is illustrated in FIG. 2 as the connector 60. The transfer set in one embodiment is a MiniSet™ manufactured by the BAXTER INTERNATIONAL INC. Although the MiniSet™ 60 is one operable embodiment of the transfer set or catheter device, the connector 10 can operate with any type of device that couples to a tube or catheter, which inserts into the patient's peritoneal cavity.

In FIG. 2, the tip protector 42 is unsecured or removed from the shell 36 of the connector 10. The port 40 of the shell 36 of the connector 10 is illustrated as sealingly connecting to a flexible tube 64 that runs to the dialysate container or bag.

FIG. 3 illustrates that after inserting the connector 10 onto the connector or transfer set 60, the shell 36 connected to the tube 64 threads off of and away from the cap 12. The connector 10 threads onto the connector or transfer set 60 using the internal threads 22 defined by the body 14 of the cap 12, which are exposed when the tip protector 42 is removed.

FIG. 3 illustrates a point in the process when the patient has completed the transfer of the dialysate from the dialysate container into the peritoneal cavity. Or, FIG. 3 illustrates a point in the process when the patient or user has finished draining spent dialysate from the peritoneal cavity into the dialysate container. In either situation, when the shell 36 threads off of the container 10, the cap 12 of the container 10 remains fixed to the connector or transfer set 60 and thereby caps off the transfer set 60. In this manner, because the sterility of cap 12 is maintained and cap 12 remains functional, a separate cap which would normally have to be taken off and re-placed onto the transfer set 60 before and after each use is no longer necessary.

Figure 4:
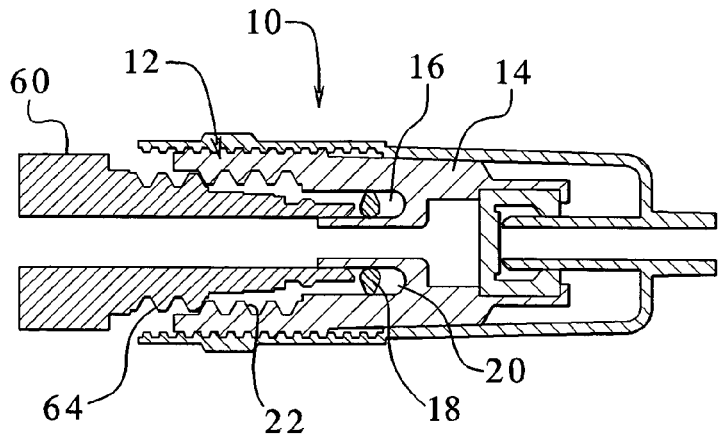
FIG. 4 is an elevation view illustrating one step for using the connector and cap of the present invention to insert and/or remove a medical fluid into/from a patient.

Referring now to FIGS. 4 to 7, one embodiment of a method for removing spent dialysate and inserting new dialysate into a patient in a substantially sterilized environment is illustrated. FIG. 4 illustrates a point in the process when the tip protector 42 has been removed and the transfer set or connector 60 is ready to be connected to the connector 10. At this point, the connector or transfer set 60 has not engaged the seal 18 to thereby rupture or displace the seal, which displaces the disinfectant 20. The connector or transfer set 60 includes external threads 64 that mates with the internally facing threads 22 of the body 14 of the cap 12.

Figure 5:
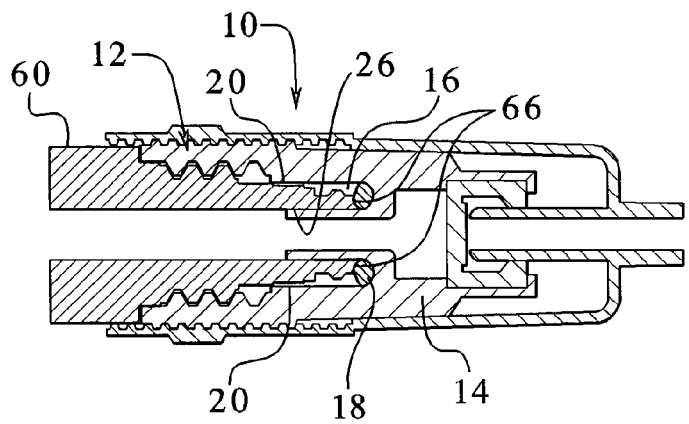
FIG. 5 is an elevation view illustrating another step for using the connector and cap of the present invention to insert and/or remove a medical fluid into/from a patient.

When the user or patient desires to connect the catheter from the peritoneal cavity to the connector 10, the user or patient threads the connector or transfer set 60 (connecting to the catheter extending to the peritoneal cavity) into the body 14 of the cap 12 so that ends 66 of the connector transfer set 60 engage the seal 18 and either move it or rupture it (best seen in FIG. 5). That is, the ends 66 apply a translational force to the seal 18 which causes the seal 18 to compress against the disinfectant 20. Eventually, as the user screws the connector 60 into the body 14, the pressure becomes too much for the seal to handle, whereby the seal either moves so that the disinfectant leaves the receptacle 16 and squirts out around the seal 18 and the ends 66 pierce, or the seal ruptures (thin sheet seal embodiment described above) and the disinfectant 20 runs out over the external threads 64 of connector 60.

In the illustrated embodiment, the seal 18 remains intact but moves or displaces the disinfectant 20 to run out over the outside of the threads 64 of the connector 60, so that microorganisms contained thereon are substantially destroyed. The seal 18 as illustrated may be made in a teardrop-type shape wherein the blunt end of the teardrop has more sealing force than the tapered or sharper end of the seal 18. In this manner, the sharper or tapered end may slightly deform as the blunt end is dragged along the surface of the receptacle 16.

The mating connector 60 in an embodiment is sized to engage and slide along the passage 26 of the body 14. This also aids in dispersing the disinfectant 20 onto the outside of the mating connector 60 to disinfect the engaging threads. That is, the disinfectant will take the path of least resistance and tend to move into the open cavity defined between the outside of the connector 60 and an inner wall of the body 14, rather than squeezing through the friction fit between the inner opening of the connector 60 and the passage 26.

Figure 6:
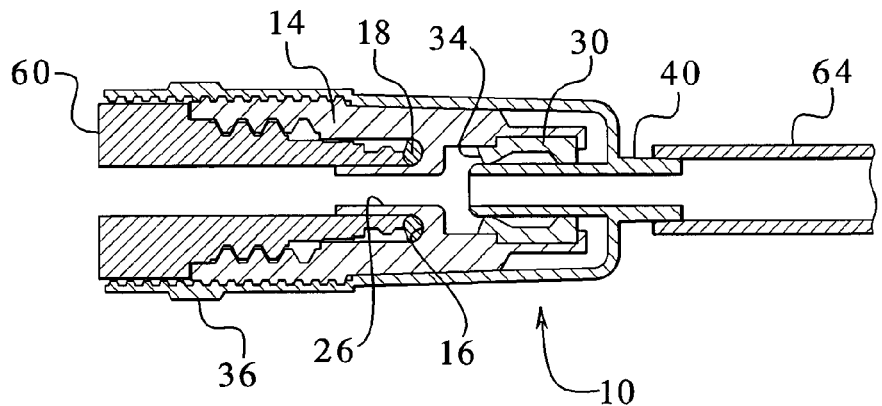
FIG. 6 is an elevation view illustrating a further step for using the connector and cap of the present invention to insert and/or remove a medical fluid into/from a patient.

Referring now to FIG. 6, after the mating connector or transfer set 60 bottoms out against the body 14, i.e., pushes the seal 18 all the way against the receptacle 16 of body 14. The assembly of the connector 10 to the mating connector 60 is now complete, so that the sealed end of the body 14 made by the slit septum 30 can be unsealed or opened. To break the seal of the septum 30, the user or patient rotates the shell or shell 36 relative to the body 14 wherein the threads of the shell 36 turn against the threads of the body 14. The shell 36 thereby translates towards the mating connector 60, so that the tube or port 40 of the shell 36 pierces through the back wall 34 of the septum 30 and through the slit defined by the back wall 34. At this point, fluid communication exists between the peritoneal cavity of the patient and the dialysate bag.

Thus, at the point illustrated in FIG. 6, the dialysate fluid may flow in either direction. That is, if the patient is removing spent dialysate from the peritoneal cavity, the dialysate fluid can flow from the catheter in the cavity into the mating connector 60, through the passage 26 of the body 14, out the port 40 and into the flexible tube 64 running to the dialysate container or bag.

In CAPD, to remove the spent dialysate from the peritoneal cavity, the user or patient typically opens a clamp on the upstream side of the mating connector 60 or integrally formed with the mating connector 60, wherein the spent dialysate runs into an awaiting container. The flex tube 64 typically runs to a "Y" connection, wherein one leg extends to the spent dialysate container and another leg extends to a new dialysate bag. When the old dialysate has been drained into the spent bag, the operator opens a fill-bag clamp that enables the new dialysate to run from the flexible tube 64, to the port 40, through the septum 30, through the passage 26, into the internal diameter of the mating connector 60 and into the catheter leading into the peritoneal cavity. With APD, one or more pumps automatically pull the spent dialysate from the patient's peritoneal cavity and places fresh dialysate into same.

FIGS. 4, 5 and 6 illustrate one complete cycle of flushing old or spent dialysate and replenishing new dialysate into the peritoneal cavity. With both CAPD and APD, the cycle is repeated a number of times. Obviously, many other different types of medical fluids may be substituted for the dialysate described herein, wherein a number of medical procedures may be performed using the connector 10 having the cap 12 of the present invention.

Figure 7:
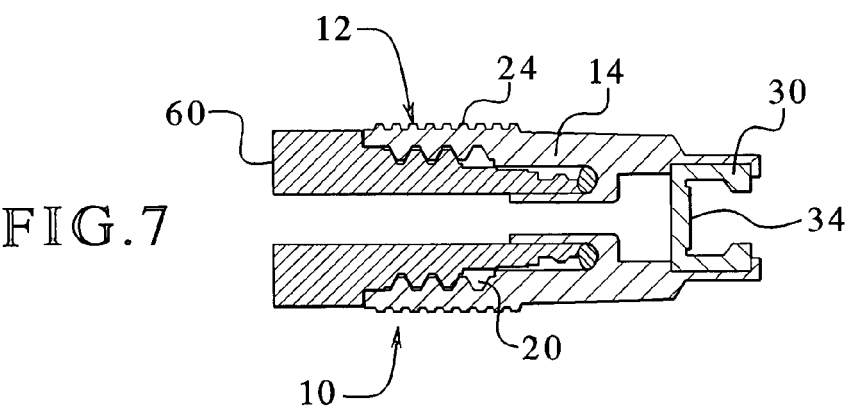
FIG. 7 is an elevation view illustrating still another step for using the connector and cap of the present invention to insert and/or remove a medical fluid into/from a patient.

Referring now to FIG. 7, when the transfer of fluids has been exchanged, the user or patient removes the shell 36 from the cap 12, so that the tube 40 of the shell 36 is removed from the septum 30. When removed, the slit in the wall 34 of the septum 30 closes and the end of the body 14 is once again sealed. The body 14 remains in the threaded position with respect to the mating connector 60, so that the disinfectant 20 is maintained between the mating threads and the open area between the mating connector 60 and the body 14.

Improved Transfer Set End for Engaging and Moving Disinfectant Seal

Figure 8:
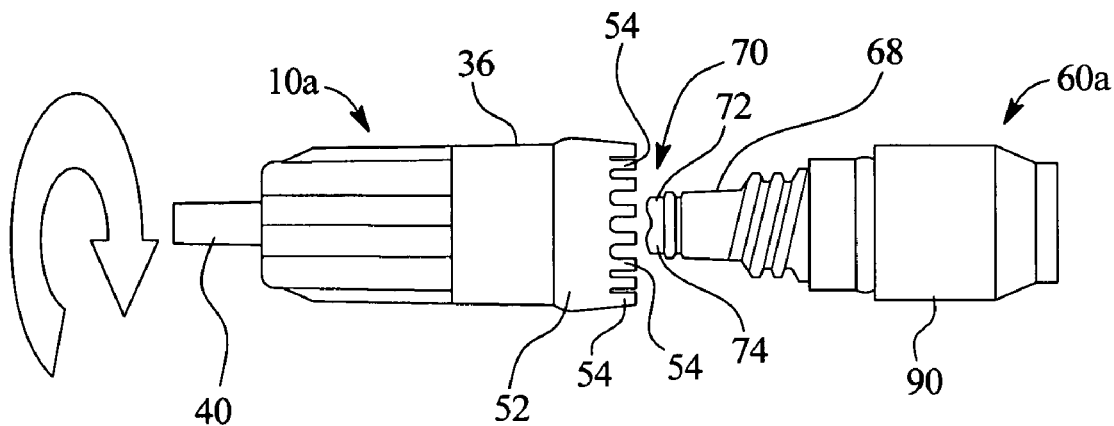
FIG. 8 is an exploded elevation view illustrating one preferred transfer set end for moving a disinfectant housing seal within the dialysate connector and for providing tactile, visual and/or audio feedback to the patient.

Referring now to FIG. 8, an improved end 70 for engaging and moving seal 18 located within a dialysate connector 10a is illustrated. End 70 is contoured to include projections or protruding portions 72 and 74. Protruding portions 72 and 74 focus the force applied by transfer set 60a to seal 18 when dialysate connector 10a and transfer set 60a are mated. Protruding portions 72 and 74 reduce the amount of operating torque needed to screw dialysate connector 10a and transfer set 60a together to move seal 18 completely and dispense all or substantially of the disinfectant residing previously within receptacle 16 located within dialysate connector 10a.

Seal 18 needs to move and/or rupture for the disinfectant to be released from within receptacle 16. Seal 18 also needs to survive relatively extreme conditions to which dialysate connector 10a is subjected. For example, dialysate connector 10a may be steam sterilized. Seal 18 must withstand such sterilization or potentially a different type of sterilization. Seal 18 should not be so robust however that a patient with reduced strength and/or dexterity cannot move seal 18 with relative ease.

Improving the force transfer from end 70 of transfer set 60a to seal 18 helps to strike a workable and proper balance. That is, protruding portions 72 and 74 aid the patient in the moving or disrupting seal 18, which allows for easier displacement of the disinfecting gel located within receptacle 16. At the same time, the torque required to assemble connector 10a to transfer set 60a is also reduced.

The non-uniform contour of end 70 of male threaded portion 68 of transfer set 60a also tends to prevent seal 18 from adhering to end 70. The adhering or sticking of seal 18 to the end of the transfer set 60a is more likely to occur if the end of portion 68 is flat. A flat end is prone to forming one or more negative pressure pocket between the end and seal 18 when forced against seal 18. Protruding portions 72 and 74 of end 70 prevent or substantially prevent such pockets from forming. Further, contoured end 70 including projecting portions 72 and 74 reduces adhesion between the seal 18 and end 70 by (i) reducing the pressure generated by end 70 on seal 18 and by (ii) reducing a surface tension between seal 18 and end 70.

Protruding portions 72 and 74 are molded readily onto or into male threaded portion 68 of transfer set 60a. While two projecting portions 72 and 74 are illustrated, end 70 may have any suitable number of such portions. In the illustrated embodiment, projecting portions 72 and 74 are generally sinusoidal in shape. In alternative embodiments, projecting portions 72 and 74 of end 70 are shaped differently to have a desired form.

Medical Fluid Connector with Retention and Feedback Feature

Figure 9:
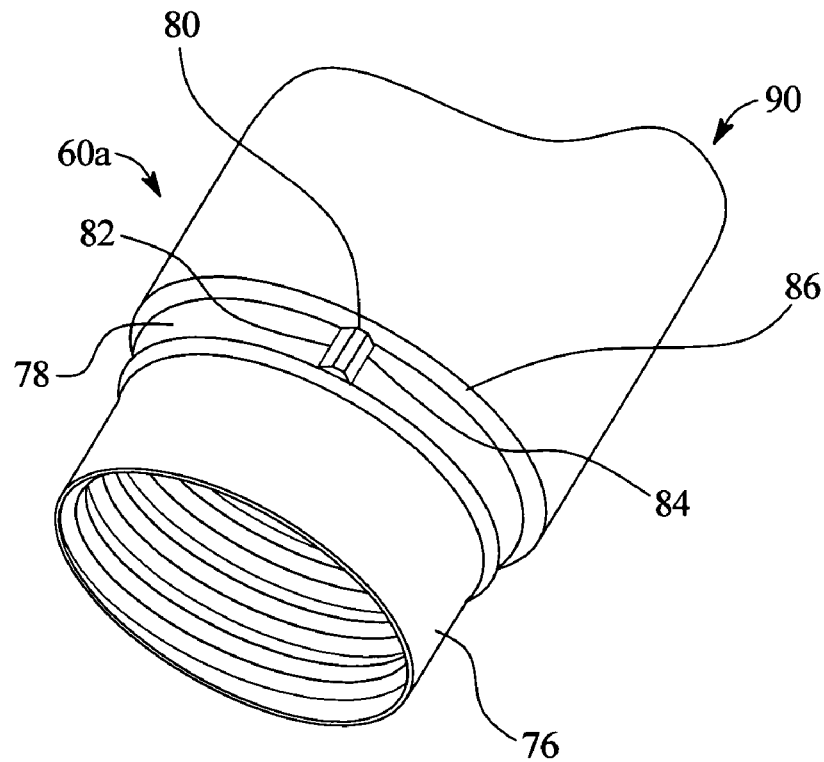
FIG. 9 is a perspective view of a portion of the transfer set shown in FIG. 8.
Figure 10:
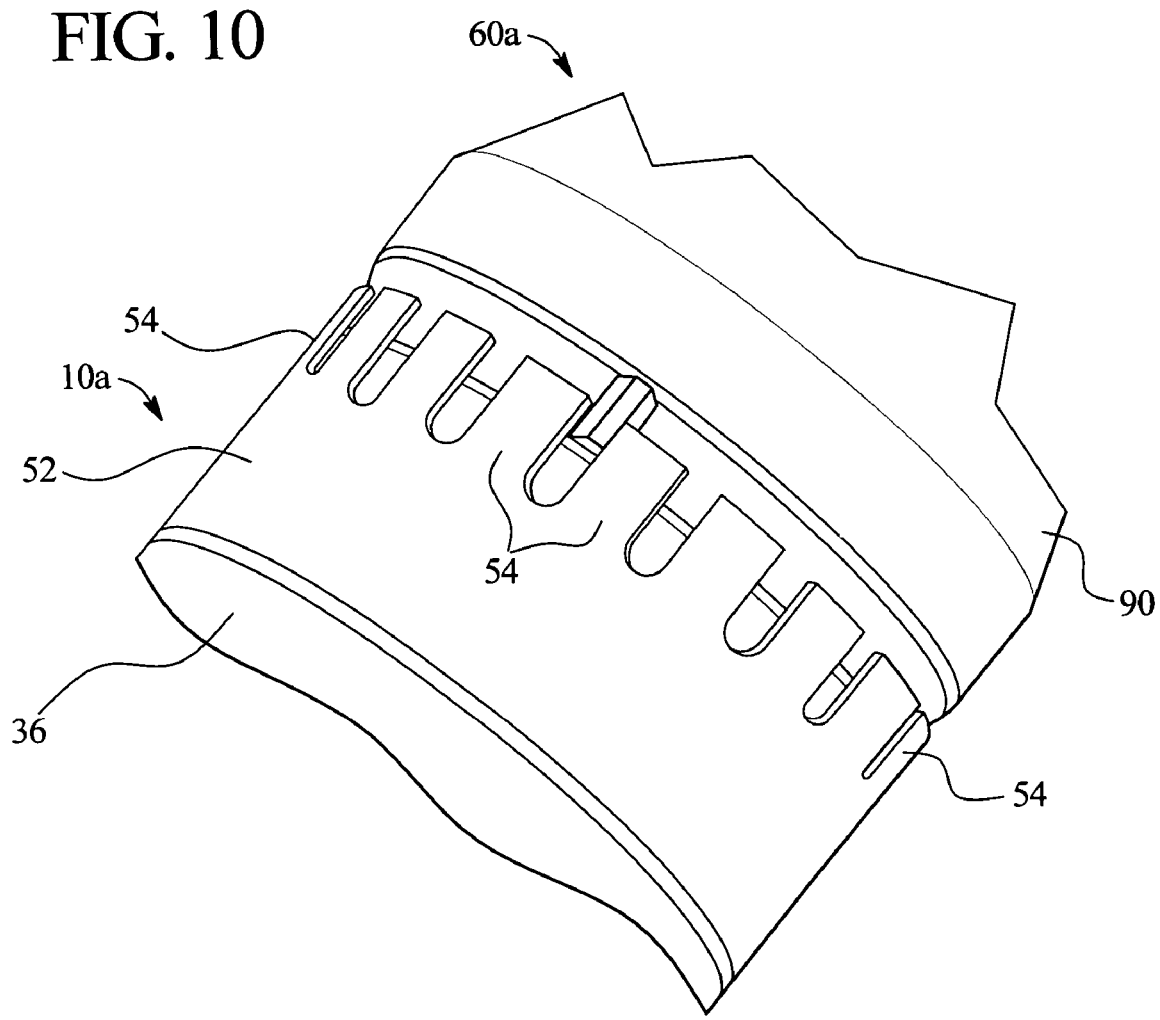
FIG. 10 is a perspective view of the dialysis connector and transfer set of FIG. 8 when engaged.

Referring now to FIGS. 8 to 10, one embodiment for providing a dialysate and transfer set assembly retention and feedback feature is illustrated. Shell 36 of dialysate connector 10a includes a head 52. Head 52 defines or includes a plurality of teeth 54 as seen in FIGS. 8 and 10. Teeth 54 extend at least substantially longitudinally from head 52. That is, teeth 54 extend in a direction that is at least substantially parallel to a centerline or line of connection between the dialysate connector 10a and transfer set 60a.

FIG. 9 illustrates that transfer set 60a includes a ring portion 76. For illustration purposes, male threaded portion 68 of transfer set 60a is removed from transfer set piece 90 to reveal ring 76. A rib 78 projects from ring 76. One or more ramps or projections 80 projects from rib 78. In one embodiment, a plurality of ramps 80 are distributed intermittently about the circumference of rib 78.

Ramp 80 includes an insertion face 82 and a removal face 84. FIG. 10 illustrates head 52 of shell 36 threaded onto ring 76 of transfer set 60a. As head 52 moves longitudinally and radially over ring 76, fingers 54 contact and abut rib 78. Rib 78 provides a slight interference fit between transfer set 60a and fingers 54 of head 52 of dialysate connector 10a. The slight interference fit helps to prevent dialysate connector 10a from coming loose from transfer set 60a during treatment. Rib 78 also provides tactile feedback to the patient to signal that the connection between dialysate connector 10a and transfer set 60a is nearing completion.

Ramps 80 provide a retention benefit as well as feedback to the patient. As illustrated by FIGS. 9 and 10, when the patient turns connector 10a, head 52 and teeth 54 clockwise about rib 78 and ramps 80 of transfer set 60a, a leading edge of teeth 54 engages the ramp insertion face 82 of ramp 80 radially. The angle of ramp insertion face 82 provides an increasing amount of tactile feel to the patient. Eventually, the tooth 54 slides completely over face 82 of ramp 80 and snaps downward along face 84 and against rib 78. Now, the following edge of tooth 54 is locked against ramp removal face 84 of ramp 80. The snapping of tooth 54 provides further tactile and potentially audible feedback to the patient. The patient can also visually see that the tooth 54 has moved over ramp 80.

It should be appreciated that transfer set 60*a* in one embodiment includes a plurality of ramps 80 and that multiple teeth 54 can make tactile and retention contact with multiple ramps 80 simultaneously, substantially simultaneously or at different times as the connector 10*a* and transfer 60*a* are threaded together. Furthermore, multiple teeth 54 will pass over the same ramp 80, providing feedback over a period of time.

Transfer set 60*a* also includes a stop or shoulder 86. Stop or shoulder 86 prevents connector 10*a* from being over-tightened to transfer set 60*a*. Ring 76, rib 78, stop or shoulder 86 and the internal threads illustrated in FIG. 9 can all be made as part of a single integral piece 90. Piece 90 in one embodiment is metallic. Alternatively, piece 90 of transfer set 60*a* is made of a polymer or plastic.

When the patient is using a CAPD or APD system and is ready to connect dialysate connector 10*a* to the transfer set 60*a*, the patient first removes a tip protector, such as tip protector 42 shown in FIGS. 1A to 1C and FIG. 2 from the dialysate connector. Tip protector 42 is removed from the shell 36 of connector 10*a*. Removing such tip protector exposes the head 52 and teeth 54 of shell 36 of dialysate connector 10*a*.

Next, the old cap (from the old dialysate connector) is removed from the transfer set. For example, FIG. 3 shows cap 12 connected to transfer set 60. As described herein, a dialysate connector 10 initially houses cap 12. Once shell 36 is pulled away from a transfer set 60, cap 12 remains on the transfer set. To insert a new dialysate connector 10, the previously used cap 12 is removed. The transfer set 60 (referring collectively to set 60*a*, etc.) is then inserted into the dialysate connector 10 (referring collectively to set 10*a*, etc.). As set 60 and connector 10 are threaded together, clicks are heard, felt and seen when teeth 54 engage and snap over the protrusions or ramps 80 located on the rib portion 78 of ring 76.

In an embodiment, ramp removal face 84 is also angled although at a different angle than ramp insertion face 82. To remove shell 36 from transfer set 60*a*, the teeth 54 are rotated counterclockwise over the differently angled, e.g., more steep ramp face 84. The pitches or angles of the faces 82 and 84 of projections 80 result in a desirable insertion and removal torque, e.g., for patients having poor dexterity and low strength.

When a connection between the dialysate connector 10*a* and transfer set 60*a* is completed, projections 80 rest between gaps located between teeth 54, locking shell 36 in place and preventing free rotation of same. Such feature minimizes inadvertent separation of the connector 10*a* and set 60*a* if for example connector 10*a* and/or transfer set 60*a* are placed under stress.

The present invention includes a number of alternatives to the embodiment illustrated in FIGS. 8 to 10. First, projections or ramps 80 may be located in any frequency about rib 78 of piece 90. There may be one projection 80 for every several teeth 54, one projection 80 for every couple of teeth 54 or one projection for each tooth 54, for example. In an embodiment, projections 80 are provided in a sufficient frequency to produce a ratchet-type connection, in which the patient feels and/or hears multiple clicks as the two pieces are threaded together. In an embodiment, the ramp projections 80 are provided back to back or virtually back to back so that in essence, rib 78 becomes a ring of ramped projections 80. Alternatively, rib 78 is not provided. Instead, a series of projections 80 extends directly from the diameter of ring 76.

Projections 80 may have any suitable shape and are not limited to the ramp faces 82 and 84 shown in FIG. 9. Projections 80 may for example be gear-shaped, generally rectangular, generally triangular, have one or more curved edges and/or one or more angled edges. The angles and/or curves are chosen to provide a desired amount of resistance that balances the need for a retention force and tactile feedback with the fact that persons with limited strength may be assembling connector 10*a* to the transfer set 60*a*.

In a further alternative embodiment, a ramped shaped projection is provided, however, the ramp projects longitudinally upward from ring 76 towards stop 86 instead of radially up and down as shown in FIG. 9. In still a further alternative embodiment, shell 36 provides inwardly facing teeth and ring 76 or rib 78 defines indents or detents that mate with such inwardly facing teeth.

Figure 11:
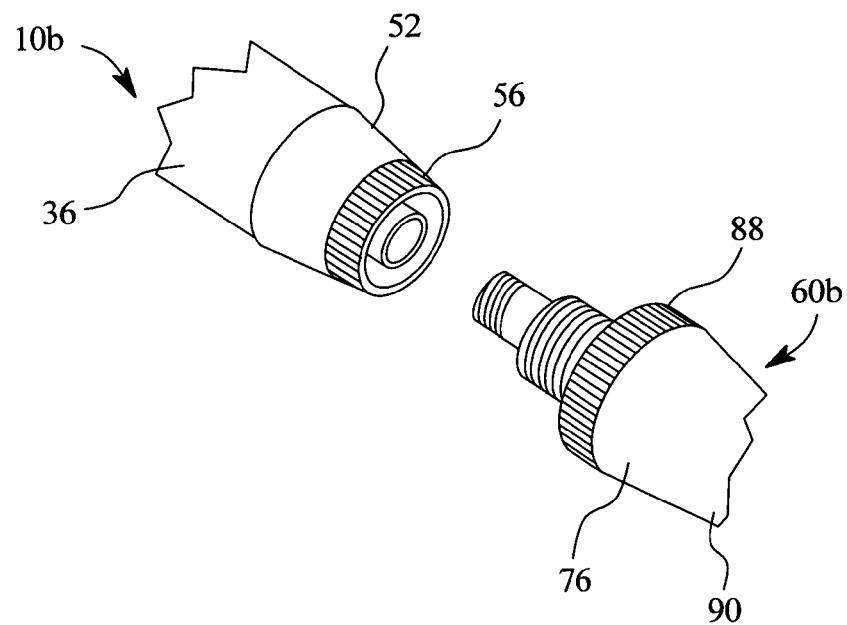
FIG. 11 is an exploded perspective view of an alternative dialysis connector and transfer set having an alternative apparatus for providing audio, visual and/or tactile feedback.

Referring now to FIG. 11, an alternative dialysate connector 10*b* and an alternative transfer set 60*b* are illustrated. The connector 10*b* and transfer set 60*b* provide a ratchet-like tactile feedback to the user or patient. Dialysate connector 10*b* includes a head 52, like connector 10*a* of FIGS. 8 to 10. Here, however, head 52 includes or defines a plurality of outwardly extending ratchet-like projections 56. Projections 56 are provided in lieu of the longitudinally extending teeth 54 of connector 10*a* in FIGS. 8 to 10.

Transfer set 60*b* includes a piece 90 having a ring portion 76. Ring portion 76 includes or defines a plurality of inwardly facing ratchet-like projections or teeth 88. Inwardly facing projections 88 mate with outwardly extending projections 56 in a ratchet-like manner to provide tactile feedback to the user or patient, e.g., to let the patient know that a connection between connector 10*b* and transfer set 60*b* is almost or totally complete. The ratchet-like connection also provides a retention force to help hold the connector 10*b* and transfer set 60*b* together when mated.

In an alternative embodiment, dialysate connector 10*b* may include inwardly facing ratchet-like teeth, while the transfer set 60*b* includes or defines outwardly facing ratchet-like teeth. The ratchet-like teeth may be generally triangular in cross-section or have any suitable cross-sectional shape.

Figure 12:
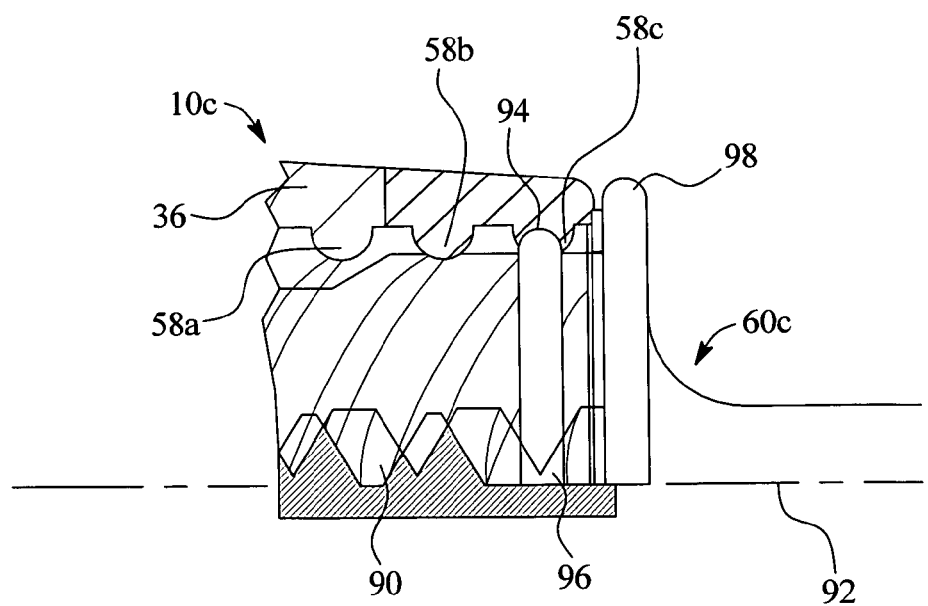
FIG. 12 is a sectioned elevation view of an assembled dialysate connector and transfer set illustrating a further alternative embodiment for providing audio, visual and/or tactile feedback to the patient.

Referring now to FIG. 12, a further alternative embodiment of the present invention is illustrated by dialysate connector 10*c* and transfer set 60*c*. For convenience, the relevant portion of shell 36 of dialysate connector 10*c* and a relative portion of transfer set 60*c* are illustrated. Shell 36 of transfer set 10*c* includes a plurality of inwardly facing projections 58*a* to 58*c*. Projections 58*a* to 58*c* may or may not be part of a thread that threads onto mating threads of transfer set 60*c*.

In the illustrated embodiment, projection 58*c* extends inwardly and annularly within shell 36 of connector 10*c*. Projection 58*c* is oriented in an embodiment in a plane that is substantially perpendicular to a center of axis 92 extending through transfer set 60*c* and shell 36. That orientation enables an undercut 94 formed in projection 58*c* to ride along a projection 96 extending outwardly from piece 90 of transfer set 60*c*. Undercut 94 includes a female contour that at least substantially matches a male contour of outwardly extending projection 96.

In operation, shell 36 of connector 10*c* threads onto transfer set 60*c* until undercut 94 of projection 58*c* mates with outwardly extending projection 96 of piece 90 of transfer set 60*c*. Piece 90 of transfer set 60*c* also includes a hardstop 98 that precludes shell 36 from being over-tightened, in which case undercut 94 could spin off of outwardly extending projection 96. The interface between undercut 94 and projection 96 provides tactile feedback to the patient or user. Additionally, the mated pieces help to hold shell 36 in place with respect to transfer set 60c when fully mated onto the transfer set.

Figure 13:
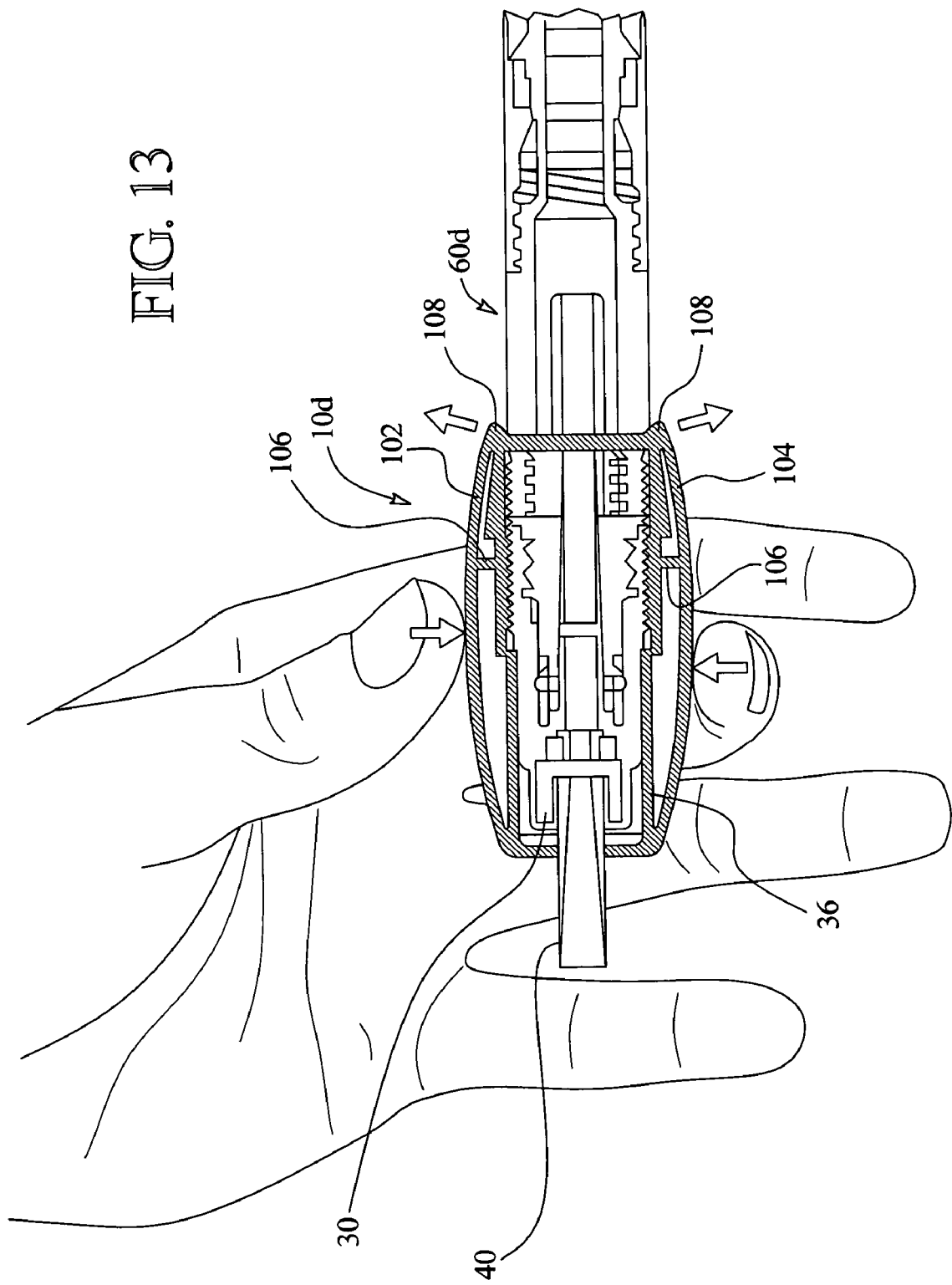
FIG. 13 is a sectioned elevation view of an assembled dialysate connector and transfer set illustrating yet a further alternative embodiment for providing audio, visual and/or tactile feedback to the patient.

Referring now to FIG. 13, a further alternative embodiment of the present invention is illustrated by dialysate connector 10d and transfer set 60d. For reference, tube 40 and septum 30 described above are shown. In this embodiment, shell 36 includes a plurality of arms 102 and 104. Arms 102 and 104 are set apart from shell 36 via standoffs 106. Standoffs 106 provide pivot points upon which arms 102 and 104 can flex. As seen in FIG. 13, arms 102 and 104 in an embodiment are bowed slightly outwardly. The patient or user presses arms 102 and 104 at the proximal side of standoffs 106. Such action causes the distal ends 108 of arms 102 and 104 to spread outwardly according to the arrows shown, so that shell 36 and connector 10d can be unthreaded from transfer set 60d.

When connector 10d is engaged with transfer set 60d, the user threads shell 36 over transfer set 60d until the distal ends 108 of arms 102 and 104 snap-fit over a protrusion or indent (not seen) provided by transfer set 60d. In essence, arms 102 and 104 lock in place on transfer 60d. Although two arms 102 and 104 are illustrated, it is also possible to have only a single arm or more than two arms. In an embodiment in which more than two arms are provided, the arms may be joined at the area where the patient presses the arms so that pressing on two sides of shell 36 (with thumb and finger as illustrated) simultaneously opens the three or more arms.

The snap-fitting of arms 102 and 104 onto transfer set 60d provides audio, visual and tactile feedback to the user that a connection is complete. The snap-fitted arms and associated projection or indentation also provide a retention function, holding shell 36 on the transfer set 60d until the patient presses the arms and twists shell 36 off of the transfer set.

Dialysate connector 10d provides a further advantage. Arms 102 and 104 can also be sized to hold tip protector 42 in place so that it cannot inadvertently come loose from the open edge of connector 10d. Viewing FIG. 1A and imaging arms extending from right to left along shell 36, it should be appreciated that the arms can be configured to snap-fit over the cylinder 48 of tip protector 42 to hold tip protector 42 in place. When the patient wishes to remove tip protector 42 from the connector, the patient presses arms 102 and 104 to release distal ends 108 of the arms from cylinder 48 of tip protector 42. The patient removes tip protector 42 from the connector with the patient's other hand.

Figure 14:
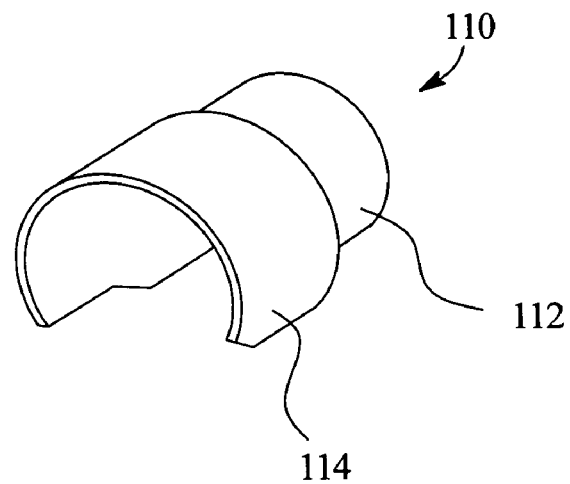
FIGS. 14 and 15 are perspective and sectioned elevation views, respectively, illustrating a locking mechanism of the present invention, which locks an assembled dialysate connector and transfer set in place.
Figure 15:
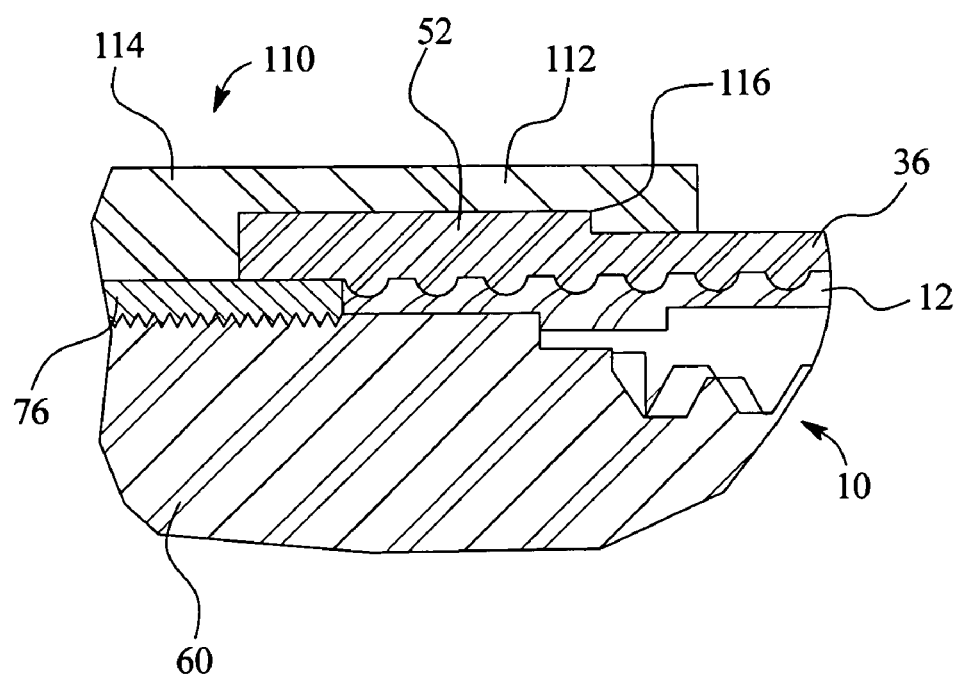

Referring now to FIGS. 14 and 15, another embodiment of the present invention is illustrated by snap-holding collar 110. FIG. 14 illustrates that snap-holding collar 110 includes a first portion 112 that snap-fits over the head 52 of shell 36. A second portion 114 of collar 110 snap-fits over the ring portion 76 of transfer set 60. Snap-holding clip 110 holds the connector 10 and transfer set 60 together after they have been mated so that the two cannot come apart during therapy. In the illustrated embodiment, collar 110 is a piece formed separately from connector 10 and transfer set 60.

In an alternative embodiment, clip or collar 110 is fixed permanently to transfer set 60. Here, viewing FIG. 15, the collar 110 would slide left to right to snap-fit over a projection or indentation 116 defined by shell 36. The sliding collar 110 is flexible enough to be pulled away from shell 36 when the shell needs to be removed from transfer set 60. The indentation of projection 116 can be made small enough and/or first portion 12 can be made pliable enough so that removing collar 110 in a sliding manner is not overly difficult.

In either the separate piece or sliding collar embodiments, collar 110 provides feedback to the patient that the connector 10 and transfer set 60 are fully mated. That is, collar 110 will not fit properly if connector 10 and transfer set 60 are not mated properly. Also, collar 110 helps to hold connector 10 and transfer set 60 together after they are fully mated. In this capacity collar 110 serves a retention function.

Figure 16:
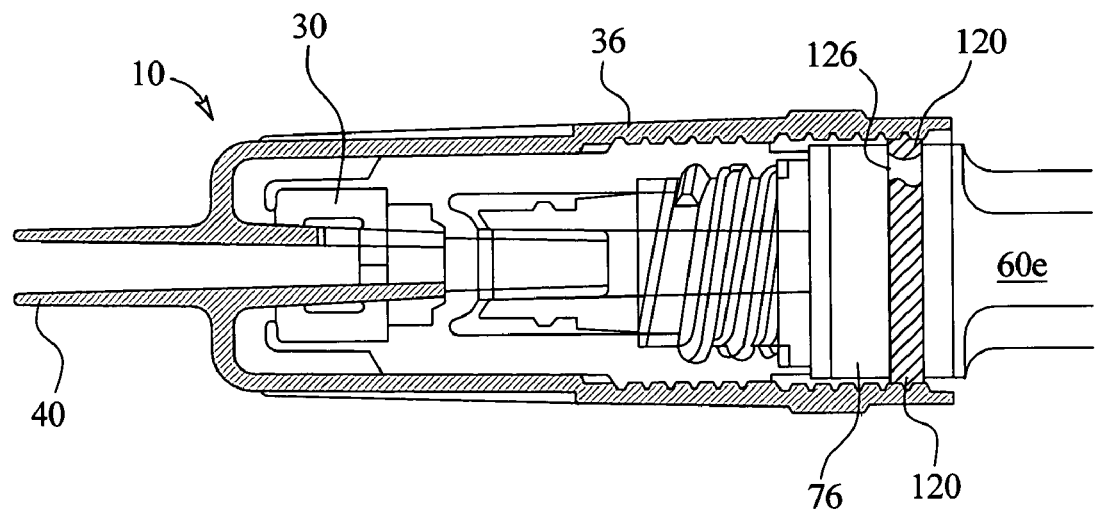
FIGS. 16 and 17 are sectioned elevation views of assembled dialysate connectors and transfer sets illustrating further alternative embodiments for providing assembly retention and feedback to the patients, which include the use of a gasket.
Figure 17:
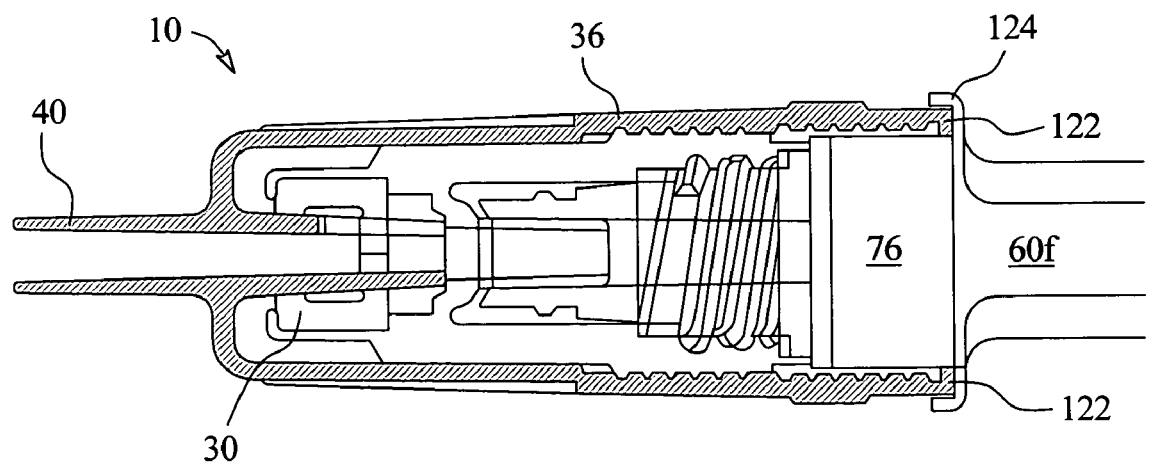

Referring now to FIGS. 16 and 17, other embodiments of the present invention are illustrated. Both embodiments of FIGS. 16 and 17 employ a gasket. Also, both embodiments employ dialysate connector 10, such as connector 10 shown in FIGS. 1A and 2 to 7. The connector of FIG. 16 provides a gasket 120 that is compressed inwardly about ring portion 76 of transfer set 60e. Alternatively, shell 36 in FIG. 17 compresses gasket 122 longitudinally against a stop 124 extending radially from ring portion 76 of transfer set 60f.

In FIG. 16, gasket 120 is housed within an annular groove 126 defined in ring portion 76 of transfer set 60e. As illustrated, gasket 120 in an embodiment is an o-ring type gasket. Alternatively, gasket 120 is flat in cross-section or has any suitable cross-sectional shape.

Gasket 122 in FIG. 17 is housed within a shallow well defined by stop 124. In the illustrated embodiment, gasket 122 has a flat washer-type shape. In an alternative embodiment, gasket 122 has any suitable o-ring or cross-sectional shape.

Gaskets 120 and 122 provide retention resistance that helps to secure shell 36 onto transfer sets 60e and 60f, respectively. Moreover, gaskets 120 and 122 provide at least tactile and visual feedback to the patient to inform same that the assembly is at least substantially complete.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A connector set for a medical fluid comprising:
 a first connector defining a first lumen;
 a second connector defining a second lumen;
 the first and second connectors threaded together to enable the first lumen to initially communicate fluidly with the second lumen after the first and second connectors are engaged; and
 wherein the first connector defines a plurality of teeth extending at least substantially parallel to an axis of mating between the first and second connectors and the second connector defines at least one protrusion extending at least substantially radially from the second connector, the teeth engaging the protrusion to provide at least one of: (i) feedback indicating that a mating of the first and second connectors is at least substantially complete and (ii) a retention force tending to hold the first and second connectors together.

2. The connector set of claim 1, wherein one of the first and second connectors houses a disinfectant that is released when the first and second connectors are mated.

3. The connector set of claim 2, wherein one of the first and second connectors includes an end that moves a seal housed in the other of the first and second connectors to release the disinfectant, the end contoured so that the seal tends to not adhere to the end.

4. The connector set of claim 1, wherein the first connector is a dialysate connector and the second connector is a transfer set piece.

5. The connector set of claim 1, wherein the second connector also includes a stop positioned behind the protrusion, the stop prohibiting further mating of the first and second connectors.

6. The connector set of claim 1, wherein the protrusion has a ramp shape, the ramp shape increasing radially in height so as to provide an increasing force to the teeth passing over the protrusion.

7. The connector set of claim 1, which includes a plurality of protrusions that engage the plurality of teeth to provide a ratchet-like tactile feedback.

8. The connector set of claim 1, wherein one of the first and second connectors includes female threads that thread to male threads of the other of the first and second connectors.

9. The connector set of claim 1, wherein one of the first and second connectors communicates fluidly with a medical fluid supply and the other of the first and second connectors communicates fluidly with a patient.

10. The connector set of claim 1, wherein one of the first and second connectors includes a tube that translates with that connector relative to the other of the first and second connectors, the tube causing the first lumen to communicate fluidly with the second lumen.

11. The connector set of claim 1, wherein one of the first and second connectors includes an inner threaded member and an outer threaded member, the inner threaded member configured to mate with the other of the first and second connectors, the outer threaded member translating with respect to the mated first and second connectors and including the teeth or the projection.

12. A connector set for a medical fluid comprising:

a first connector defining a first fluid passage;

a second connector defining a second fluid passage;

the first and second connectors threaded together to enable the first fluid passage to initially communicate fluidly with the second fluid passage after the first and second connectors are engaged; and wherein the first connector defines a plurality of teeth extending at least substantially parallel to an axis of mating between the first and second connectors and the second connector defines at least one protrusion extending at least substantially radially from the second connector, the teeth engaging the protrusion to provide at least one of: (i) feedback indicating that a mating of the first and second connectors is at least substantially complete and (ii) a retention force tending to hold the first and second connectors together.

* * * * *